United States Patent [19]

Spence

[11] Patent Number: 4,979,953
[45] Date of Patent: Dec. 25, 1990

[54] MEDICAL DISPOSABLE INFLATABLE TOURNIQUET CUFF

[75] Inventor: Jerry L. Spence, Kirkland, Wash.
[73] Assignee: InstruMed, Inc., Bothell, Wash.
[21] Appl. No.: 481,859
[22] Filed: Feb. 16, 1990
[51] Int. Cl.⁵ .............................................. A61B 17/00
[52] U.S. Cl. ..................................... 606/202; 128/686
[58] Field of Search ............................. 606/202, 203; 128/677–686

[56] References Cited

U.S. PATENT DOCUMENTS

| | | |
|---|---|---|
| 800,467 | 9/1905 | Myers . |
| 814,795 | 3/1906 | Myers . |
| 2,347,197 | 4/1944 | LaLiberte ............... 128/327 |
| 2,511,269 | 6/1950 | Jones ........................ 128/327 |
| 3,120,846 | 2/1964 | Fletcher .................... 128/327 |
| 3,467,077 | 9/1969 | Cohen ....................... 128/2.05 |
| 3,504,675 | 7/1970 | Bishop, Jr. ................ 128/327 |
| 3,633,567 | 1/1972 | Sarnoff ...................... 128/2.05 |
| 3,654,931 | 4/1972 | Hazlewood ................ 128/327 |
| 3,669,096 | 6/1972 | Hurwitz ..................... 128/2.05 |
| 3,670,735 | 6/1972 | Hazlewood ................ 128/327 |
| 3,713,446 | 1/1973 | Sarnoff ...................... 128/327 |
| 3,756,239 | 9/1973 | Smythe ...................... 128/327 |
| 3,906,937 | 9/1975 | Aronson .................... 128/2.05 |
| 3,930,506 | 1/1976 | Overend .................... 128/327 |
| 3,946,731 | 3/1976 | Lichtenstein .............. 128/214 |
| 3,968,788 | 7/1976 | Hopkins .................... 128/2.05 |
| 3,977,393 | 8/1976 | Kovacic .................... 128/2.05 |
| 3,985,123 | 10/1976 | Herzlinger et al. ....... 128/2.05 |
| 4,106,499 | 8/1978 | Ueda ......................... 128/2.05 |
| 4,149,540 | 4/1979 | Hasslinger ................ 128/327 |
| 4,177,813 | 12/1979 | Miller et al. .............. 128/326 |
| 4,321,929 | 3/1982 | Lemelson et al. ........ 128/630 |
| 4,326,513 | 4/1982 | Schulz et al. ............. 128/203.14 |
| 4,354,503 | 10/1982 | Golden ..................... 128/686 |
| 4,406,281 | 9/1983 | Hubbard et al. .......... 128/132 |
| 4,465,076 | 8/1984 | Sturgeon ................... 128/686 |
| 4,635,635 | 1/1987 | Robinette-Lehman ..... 128/327 |

Primary Examiner—C. Fred Rosenbaum
Assistant Examiner—William W. Lewis
Attorney, Agent, or Firm—Pravel, Gambrell, Hewitt, Kimball & Krieger

[57] ABSTRACT

A disposable inflatable tourniquet apparatus includes an inner inflatable bladder formed of two rectangular bladder wall members of polymer impregnated fabric peripherally welded to form a peripheral bond that develops the burst pressure of the bladder wall members. A conduit inflates the bladder, and a fabric cover is peripherally stitched at a border to the bladder at the peripheral bond. A curved stiffener plate is held inside the cover but outside the bladder, and within the stitched border.

19 Claims, 2 Drawing Sheets

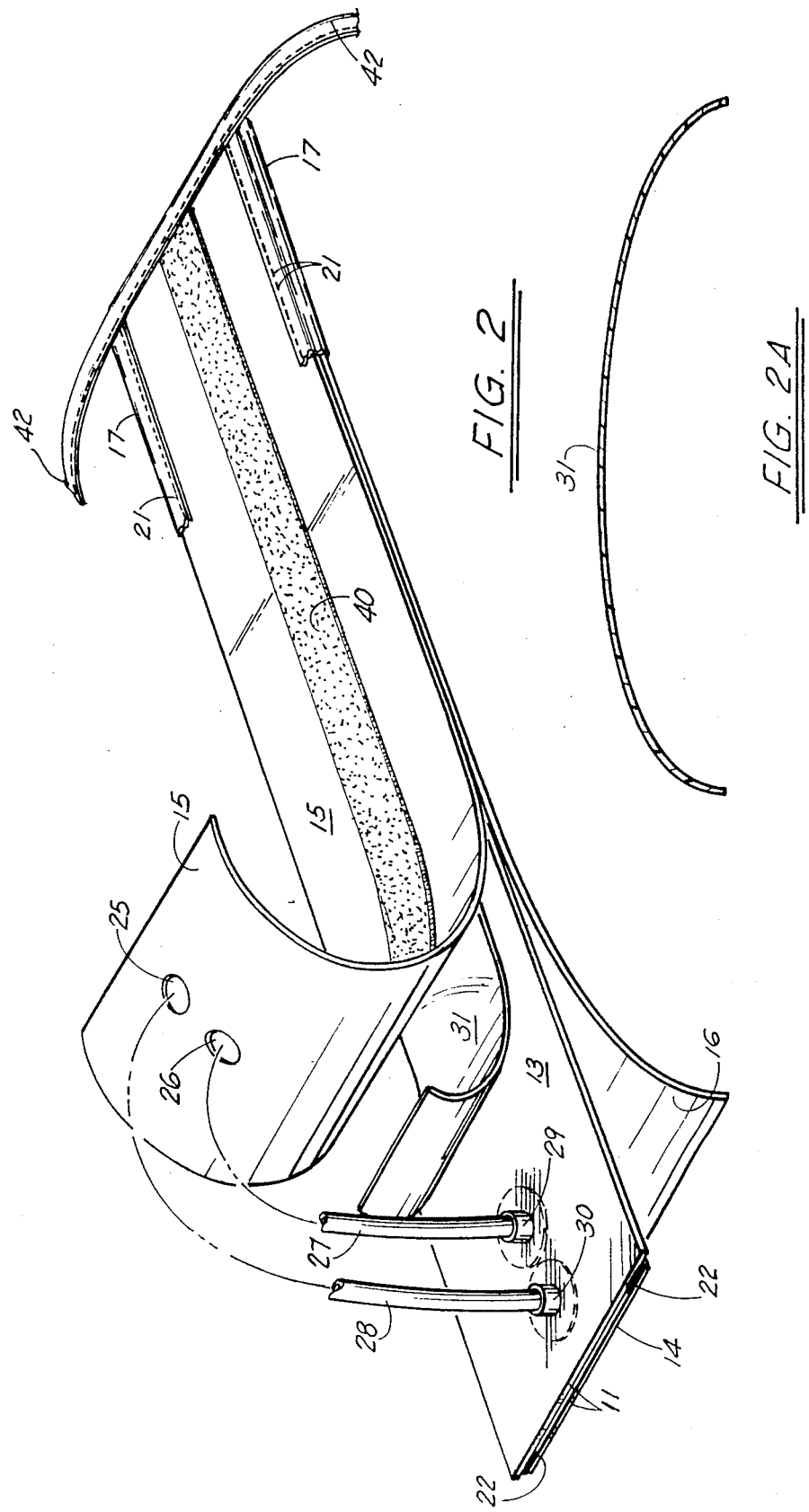

MEDICAL DISPOSABLE INFLATABLE TOURNIQUET CUFF

BACKGROUND OF THE INVENTION:

1. Field of the Invention

The present invention relates to medical tourniquets, and more particularly relates to disposable inflatable tourniquet cuffs of the type that are wrapped around an arm or leg and inflated to provide pressure for controlling blood flow.

2. General Background

Tourniquets used in the medical industry are often inflatable, and are comprised of an internal bladder which is usually molded rubber that is contained within a cover. The cover prevents ballooning or over expansion of the internal rubber bladder. The cover is usually removable so that it can be cleaned after each use. However, sterility is a problem with reusable tourniquets.

Some patents have issued for disposable tourniquets that are also inflatable. Disposable tourniquets are attractive because they eliminate the need for cleaning which is a critical problem because blood and other fluids and contaminants soil the cover of the tourniquet. Therefore, there is a need for a simple, easy to use, easy to construct yet durable inflatable cuff apparatus which is of high quality yet available at minimal expense.

Various prior patented tourniquet cuffs which are inflatable include U.S. Pat. No. 3,504,675, issued to W. A. Bishop, Jr.; U.S. Pat. No. 3,670,735, issued to Louis Hazelwood; U.S. Pat. No. 4,321,929, issued to Jerome Lemelson; and U.S. Pat. No. 4,635,635, issued to Cynthia Robinette-Lahman. The '635 Robinette-Lahman patent relates to an improved tourniquet which is inflatable and adapted to be wrapped around a body part. The '635 Robinette-Lahman cuff apparatus includes an inner bladder of a pair of layers and three other outer cover layers that are sealed at the edges using multiple radio frequency welds. One layer placed intermediate the bladder and cover is used for containing a stiffener. The '635 Robinette-Lahman patent uses numerous radio frequency welds including a first weld which seals the edges of the bladder, and additional welds which seal the bladder to the cover parts and to the additional cover which seals the stiffener.

The following patents disclose other patented tourniquets and cuffs.

| PRIOR ART | | |
|---|---|---|
| U. S. PAT. No. | INVENTOR | TITLE |
| 3,467,077 | L. Cohen | "Sphygmomanometric Cuff" |
| 4,465,076 | H. Sturgeon | "Self-Applying Accessory For Blood Pressure Cuff" |
| 3,930,506 | T. Overend | "Disposable Phlebotomists Tourniquet" |
| 3,906,937 | T. Aronson | "Blood Pressure Cuff And Bladder And Apparatus Embodying The Same" |
| 3,968,788 | J. Hopkins | "Sphygmomanometer Band And Method Of Self-Application Thereof" |
| 3,977,393 | V. Kovacic | "Pressure Cuff And Method Of Placing It On A Limb" |
| 3,713,446 | S. Sarnoff | "Self-Applied Pneumatically Actuated Pressure" |
| 3,669,096 | M. Hurwitz | "Self-Donning Sphygmomanometer Cuff" |
| 3,633,567 | S. Sarnoff | "Pneumatically Actuated Pressure Dressing" |
| 3,654,931 | L. Hazlewood | "Disposable Tourniquet Cover" |
| 800,467 | H. Meyers | "Elastic Bandage" |
| 814,795 | H. Meyers | "Elastic Bandage" |
| 4,177,813 | C. Miller et al. | "Vessel Occluder" |
| 4,149,540 | R. Hasslinger | "Separable Cinch Fastener" |
| 4,106,499 | K. Ueda | "Sphygmomanometer Cuff" |
| 4,406,281 | V. Hubbard | "Fluid Impermeable Cover For Operating Room Tourniquet" |
| 4,354,503 | R. Golden | "Blood Pressure Cuff" |

SUMMARY OF THE PRESENT INVENTION:

The present invention provides an improved medical, disposable inflatable tourniquet cuff construction wherein a single bond (preferably a radio frequency weld) peripherally joins the two bladder layers, eliminating additional parts which are required in the Robinette-Lahman patent, as well as eliminating additional radio frequency welds.

The present invention provides an improved medical disposable inflatable tourniquet cuff that is comprised of a pair of flexible opposed and correspondingly sized bladder wall members, each of a polymer impregnated fabric that can be bonded to the other, and each having inner and outer surfaces that are positioned face-to-face with the inside surface of one bladder wall member abutting the inside surface of the other and being peripherally joined at a bond formed between the inside surfaces of the peripheral edge portion of one wall member and the inside surface of the peripheral edge portion of the other bladder wall member.

An opening is provided in one of the bladder wall members and a conduit is provided for inflating the bladder at the opening. However, multiple conduits and multiple corresponding openings can be provided, such as, for example, a two conduit or a four conduit apparatus.

A pair of fabric cover members are placed respectively on opposite sides of and abutting the pair of bladder wall members. At least one outermost peripheral stitched border strip peripherally joins the cover members to the bladder wall members at the bond, the strip contacting the peripheral edge portion of each cover member, and the peripheral bond extending a distance inwardly of the stitched border. A stiffener plate member is disposed between one of the bladder walls and one of the cover members and means is provided for securing the cuff around a body part.

In the preferred embodiment, the bladder wall members are polyurethane impregnated fabric, such as a nylon fabric.

The bladder wall members are preferably peripherally joined at the peripheral bond with a radio frequency welded bond and the stitched border penetrates the bladder wall members at the bond.

BRIEF DESCRIPTION OF THE DRAWINGS:

For a further understanding of the nature, objects, and advantages of the present invention, reference should be had to the following detailed description, taken in conjunction with the accompanying drawings, in which like reference numerals denote like elements, and wherein:

FIG. 2 is a perspective, partially exploded view of the preferred embodiment of the apparatus of the present invention;

FIG. 2A is a partial sectional view of the preferred embodiment of the apparatus of the present invention illustrating the stiffener plate in its preferred shape;

Figure 1:
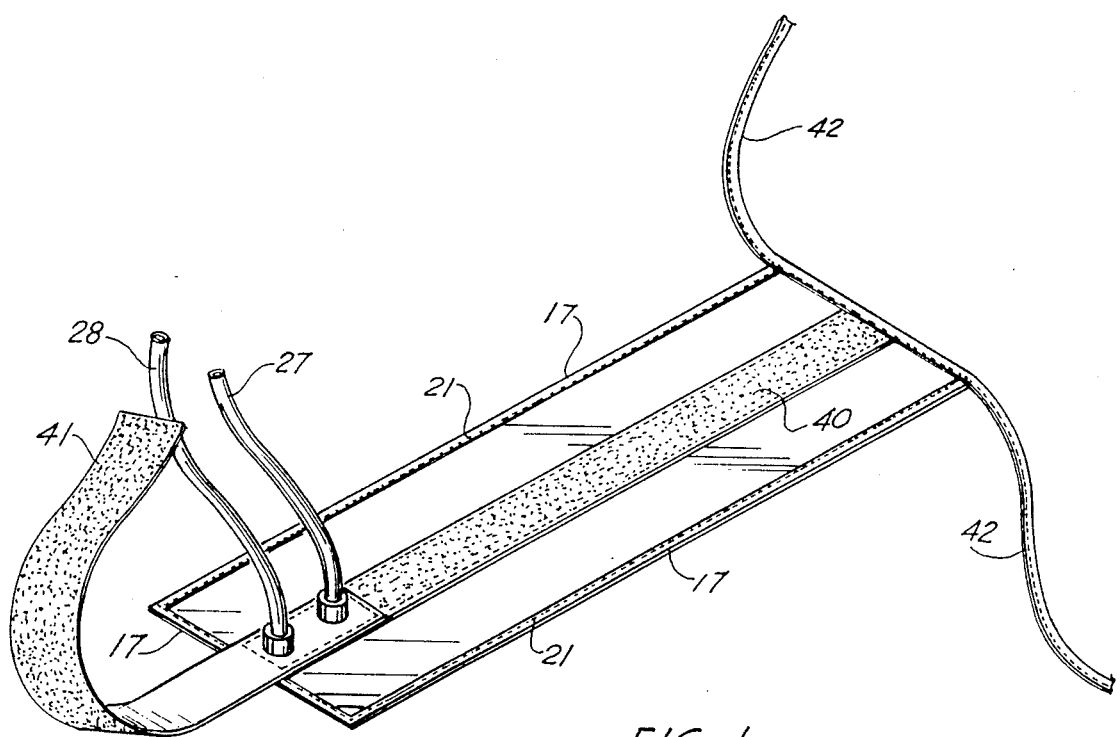
FIG. 1 is a perspective view of the preferred embodiment of the apparatus of the present invention.
Figure 3:
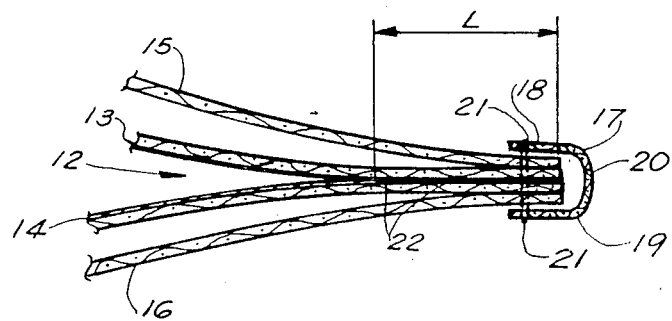
FIG. 3 is a fragmentary sectional view of the preferred embodiment of the apparatus of the present invention.

DETAILED DESCRIPTION OF THE PREFERRED EMBODIMENT:

FIGS. 1-4 show the preferred embodiment of the apparatus of the present invention designated generally by the numeral 10. Medical disposable inflatable tourniquet cuff 10 includes a layered pair of flexible, opposed, and correspondingly sized bladder wall members 13, 14 with an inflatable air space 12 formed therebetween by a bond 22. Bladder wall members 13, 14 are preferably of a polymer impregnated fabric such as a 400 Denier nylon impregnated with polyurethane. The bladder wall members 13, 14 can be bonded at their periphery using preferably high frequency welding to form a bond that extends about the periphery of each bladder wall member 13, 14, extending a distance L from the edge of each, as shown in FIG. 3.

Each bladder wall member 13, 14 has an inner surface so that the corresponding inner surfaces of each bladder wall member 13, 14 are positioned face-to-face in an abutting fashion. Openings 29, 30 are provided in one of the bladder wall members 13, 14 for attaching conduits 27, 28 thereto, with a closure valve structure being provided at the joint between each opening 29, 30 and its conduit 27, 28.

Figure 4:
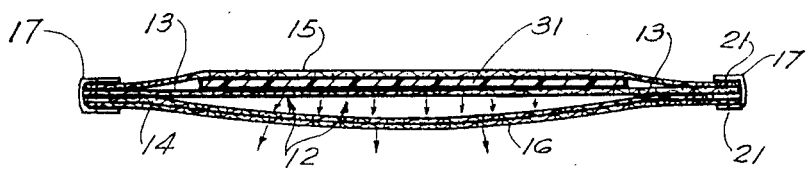
FIG. 4 is a sectional view of the preferred embodiment of the apparatus of the present invention.

A pair of fabric cover members 15, 16 are placed respectively on opposite sides of and abutting respectively the pair of bladder wall members 13, 14, as shown in FIG. 4. At least one outermost peripheral stitched border strip 17 peripherally joins the cover members 15, 16 to the bladder wall members 13, 14 at the bond 22.

Stiffener plate member 31 is disposed between one of the bladder walls 13 and one of the cover members 15. Strap 41 is provided which can be a Velcro fastener that cooperates with strip 40 for securing the cuff 10 around a body part. Ties 42 hold the strap 41 in a closed operative position after placement around a patient's body part.

The peripheral stitched border strip 17 is preferably U-shaped in cross-section, as shown in FIGS. 3 and 4. Strip 17 includes a first flat portion 18 which rests upon the peripheral edge and outer surface of the cover member 15. A second flat portion extends along the periphery of and outer surface of cover member 16, and a transverse portion 20 extends between the members 18 and 19, as shown in FIG. 4, so that a generally U-shaped border strip 17 is provided about the periphery of cuff 10, as shown in FIGS. 1, 2, 3, and 4.

Stitching 21 extends through stitched border strip 17 by penetrating the member 18, each of the cover members 15, 16, as well as each of the bladder wall members 13, 14 as shown in FIGS. 3 and 4. The stitching 21 thus penetrates both the strip 17 and each of the layers 13-16. The stitching 21 penetrates the bladder formed by bladder walls 13, 14 at the bond 22. Further, cheaper unimpregnated fabric (e.g., Nylon) can be used for the covers 15, 16 and for the border 17. In this manner, a simple inexpensive stitched arrangement can be used for assembling the entire apparatus so that only a single radio frequency bond needs to be made between the bladder wall members 13, 14. The entire apparatus is assembled by low cost yet efficient and durable stitching with fabric cover layers.

This construction provides an improved tourniquet cuff apparatus which is very strong yet very easy to make and thus can be made avilable to the patient at a very low cost.

Because the radio frequency bond 22 extends a distance L inwardly of the edges of layers 13-16, the stitching can be placed close to the edges of each layer 13-16, and thus does not destroy nor interfere with the bond 22. Thus, the bond 22 can extend a distance of, for example, one-half-one inch ($\frac{1}{2}''-1''$) inwardly of the stitched border 21 so that the stitching does not affect the burst pressure developed by the bond 22.

Conduits 27, 28 cooperate with openings 29, 30 respectively for adding air to the space 12 via openings provided in one of the bladder members 13. Corresponding openings 25, 26 are provided in cover 15, as shown in FIG. 2, for accommodating the conduits 27, 28.

In view of the numerous modifications which could be made to the preferred embodiments disclosed herein without departing from the scope or spirit of the present invention, the details herein are to be interpreted as illustrative and not in a limiting sense.

What is claimed as invention is:

1. A medical disposable inflatable tourniquet cuff, comprising:
    (a) a layered pair of flexible, opposed and correspondingly sized bladder wall members, each of an impregnated fabric that can be bonded to the other, each having inner and outer surfaces and positioned face-to-face with the inside surface of one bladder wall member abutting the inside surface of the other;
    (b) the bladder wall members being peripherally joined at a peripheral bond formed between the inside surface of the peripheral edge portion of one wall member and the inside surface of the peripheral edge portion of the other bladder wall member;
    (c) an opening in one of the bladder wall members;
    (d) conduit means for inflating the bladder at the opening;
    (e) at least one cover member placed respectively on one side of and abutting one of the bladder wall members;
    (f) at least one outermost peripheral stitched border strip for peripherally joining the cover member to the bladder wall members at the bond, the strip contacting the peripheral edge portion of the cover member;
    (g) the peripheral bond extending a distance inwardly of the stitched border so that the stitched border does not appreciably affect the burst pressure of the bladder as developed by the peripheral bond;
    (h) a stiffener plate member disposed between one of the bladder walls and the cover member; and
    (i) means for securing the cuff around a body part.

2. The disposable inflatable cuff apparatus of claim 1 wherein the bladder wall members are of a polyurethane impregnated fabric.

3. The disposable inflatable cuff apparatus of claim 2 wherein the bladder wall members are peripherally joined at the peripheral bond with a radio frequency welded bond, and the stitched border penetrates the bladder wall members at the bond.

4. The disposable inflatable cuff apparatus of claim 1 wherein the inner surface of each bladder wall member is impregnated with a material that allows bonding between the said inside surfaces by radio frequency welding.

5. The disposable inflatable cuff apparatus of claim 1 wherein the inside surfaces of the bladder wall members are impregnated with a material that allows bonding between the said inside surfaces by radio frequency welding.

6. The disposable inflatable cuff apparatus of claim 1 further comprising a peripheral border strip of material that covers the edges of the assembly of bladder wall members and the cover member.

7. The disposable inflatable cuff of claim 6 wherein the peripheral strip extends to the periphery of the exposed outer surface of the cover member.

8. The disposable inflatable cuff of claim 8 wherein the strip is generally U-shaped in cross-section.

9. The disposable inflatable cuff of claim 8 wherein the stitched border extends along and through the border strip.

10. A medical disposable inflatable tourniquet comprising:
   (a) a generally rectangular bladder comprised of a pair of flexible, impregnated fabric bladder layers, each having cooperating abutting inside surfaces that abut in face-to-face relationship, and being peripherally connected at a welded bond defining an air chamber between the bladder layers and interiorly of the bond;
   (b) the peripheral bond being an inwardly extending bond that fuses the peripheral edge portion of the inside surfaces of each bladder layer beginning at the outer edge thereof and extending a distance sufficient to develop the burst pressure of at least one of the bladder layers;
   (c) an opening in one of the bladder layers;
   (d) a conduit for inflating the bladder at the opening;
   (e) a flexible rectangular fabric cover that encapsulates the bladder, comprised of a pair of rectangular fabric cover panels positioned on opposite sides of the rectangular bladder, and connected by a peripheral stitched border that secures the pair of fabric panels to the bladder, the border including stitching that penetrates the bladder at the bond; and
   (f) means for securing the cuff around a body part.

11. The disposable inflatable tourniquet of claim 10 wherein the bladder layers are polymer impregnated fabric layers.

12. The disposable inflatable tourniquet of claim 11 wherein the inside surfaces of the fabric layers are impregnated with a polymer material.

13. The disposable inflatable tourniquet of claim 11 wherein the border includes a border strip of material that covers the edges of the bladder and the cover.

14. The disposable inflatable tourniquet of claim 10 wherein the bladder layers and cover panels are of similar dimensions so that the edges of the bladder layers and cover panels align upon assembly.

15. The disposable inflatable tourniquet of claim 13 wherein the border strip is generally U-shaped in section, and including portions that register with each of the cover panels.

16. The disposable inflatable tourniquet of claim 10 further comprising a curved stiffener panel held between the bladder and the cover and interiorly of the bond.

17. The disposable inflatable tourniquet of claim 16 wherein the stiffener panel is of a stiff plastic material.

18. The disposable inflatable tourniquet of claim 16 wherein the stiffener panel is positioned externally of the bladder between the bladder and the inner cover panel.

19. The disposable inflatable tourniquet of claim 10 further comprising a closure strap for holding the tourniquet to a patient.

* * * * *